United States Patent [19]

Ward

[11] Patent Number: 4,509,531
[45] Date of Patent: Apr. 9, 1985

[54] PERSONAL PHYSIOLOGICAL MONITOR

[75] Inventor: John W. Ward, Charlottesville, Va.

[73] Assignee: Teledyne Industries, Inc., Los Angeles, Calif.

[21] Appl. No.: 402,533

[22] Filed: Jul. 28, 1982

[51] Int. Cl.³ .............................................. A61B 5/00
[52] U.S. Cl. .................................. 128/736; 128/738; 374/142; 374/185
[58] Field of Search .................. 128/670–671, 128/734, 736, 738; 374/102, 107, 142, 163, 168, 170, 183, 185, 208, 210

[56] References Cited

U.S. PATENT DOCUMENTS

| | | | |
|---|---|---|---|
| 4,008,617 | 2/1977 | Yen et al. | 374/170 X |
| 4,031,365 | 6/1977 | Raggiotti et al. | 374/183 X |
| 4,112,764 | 9/1978 | Turner | 374/142 |
| 4,151,831 | 5/1979 | Lester | 128/736 |
| 4,178,916 | 12/1979 | McNamara | 128/736 X |
| 4,297,685 | 10/1981 | Brainard | 128/736 X |
| 4,365,637 | 12/1982 | Johnson | 128/734 |

FOREIGN PATENT DOCUMENTS 2913048 10/1980 Fed. Rep. of Germany ...... 128/736

Primary Examiner—William E. Kamm
Assistant Examiner—Francis J. Jaworski
Attorney, Agent, or Firm—Cushman, Darby & Cushman

[57] ABSTRACT

An improved personal physiologic monitor continuously monitors changes in galvanic skin resistance, temperature or both in order to detect for example the onset of a hypoglycemic state in a diabetic. Measurements are enacted over brief periodic intervals to conserve power. A temperature reference is automatically established and periodically corrected to accommodate slowly changing non-symptomatic skin temperature variations, whereas an alarm indicia is generated if the peripheral skin temperature drops a predetermined amount below the reference value.

26 Claims, 9 Drawing Figures

F I G. 2
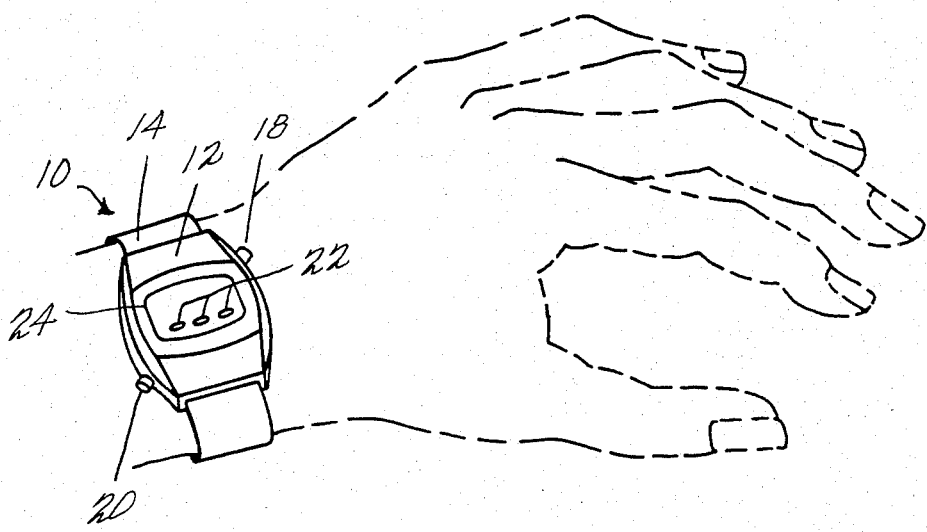
F I G. 3
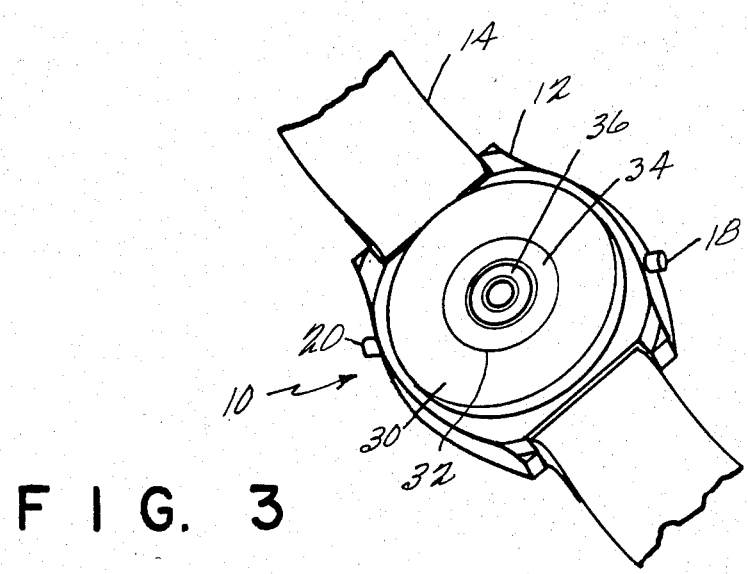

FIG. 4
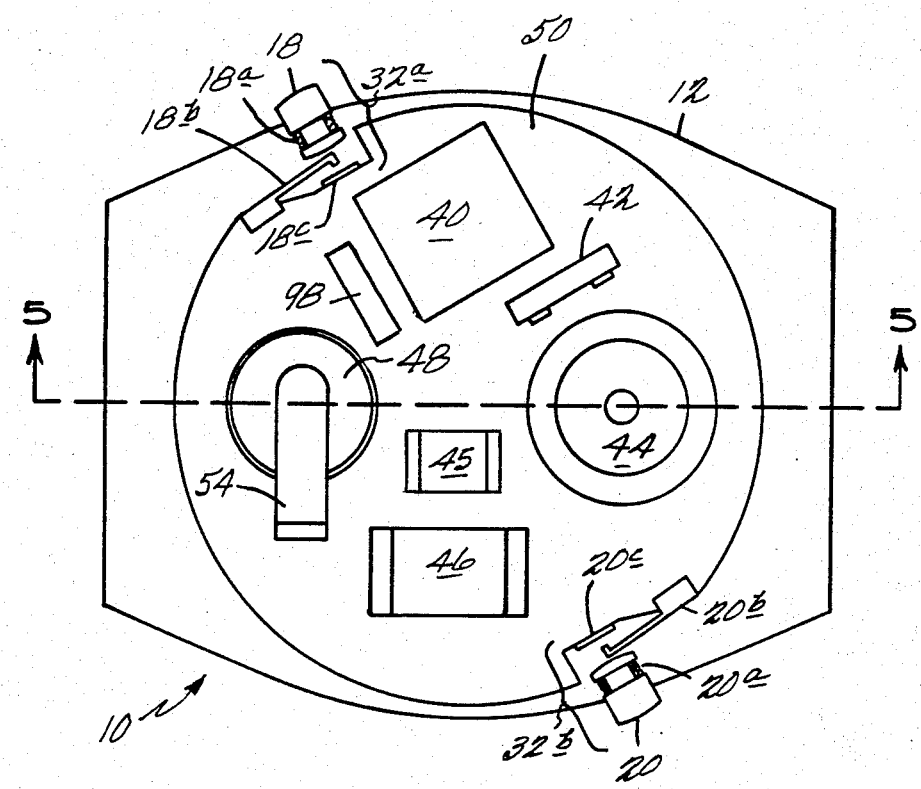
FIG. 5
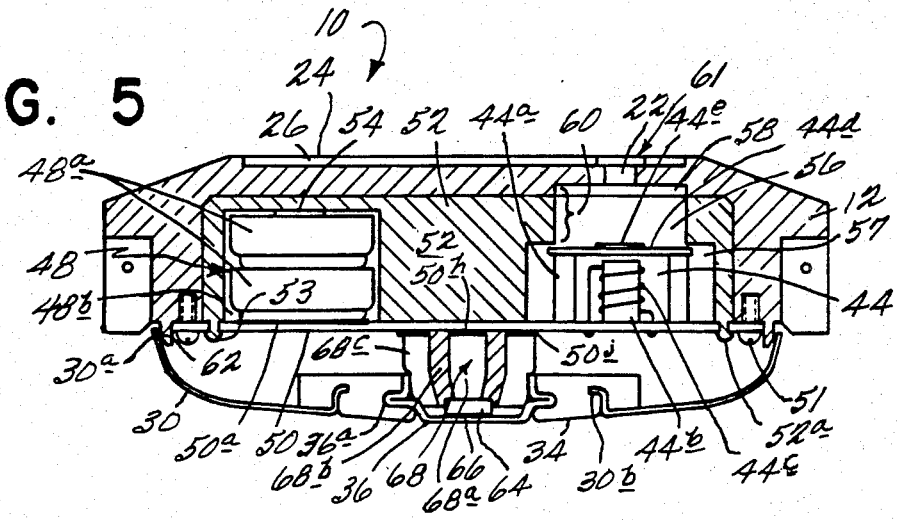
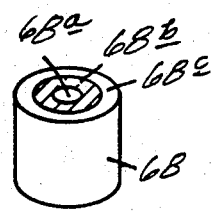
FIG. 5A

PERSONAL PHYSIOLOGICAL MONITOR

BACKGROUND OF THE INVENTION

1. Field of the Invention

The present invention relates to personal physiological monitors, and, in particular, to personal physiological monitors which detect changes in galvanic skin resistance, skin temperature, or both.

2. Description of the Prior Art

The desirability of continuously monitoring galvanic skin resistance and skin temperature is well-known. Changes in skin temperature at the extremities and the presence of perspiration on the skin surface (resulting in a decreased galvanic skin resistance) are symptomatic of various physiological conditions, such as, for example, the onset of hypoglycemia in a diabetic.

Hypoglycemia occurs in a diabetic when, for various reasons, the diabetic's blood glucose level falls below a certain value. If detected, the hypoglycemic state can readily be reversed by ingestion of orange juice or other common sources of digestable sugar. However, if undetected, the hypoglycemic diabetic enters a deep comatose state, which can result in severe brain damage or death.

A conscious adult diabetic can typically ascertain the onset of hypoglycemia by recognizing any of the various physical symptoms associated with a hypoglycemic condition, such as; a feeling of anxiety or nervousness, blurring vision, inability to focus the eyes, nausea, or unexplained perspiration. Once these symptoms are recognized, sugar can be ingested and the hypoglycemic onset can be reversed. However, if the hypoglycemic onset occurs and continues while the diabetic is asleep, or if the diabetic is, for a variety of reasons, unable to recognize such physical symptoms, he can enter a comatose state before the hypoglycemia is detected. Accordingly, since it is known that the onset of hypoglycemia is commonly evidenced by the presence of profuse perspiration, decreased skin temperature at the extremities, or both, such parameters can be monitored and alarm indicia can be generated in response to such external physical symptoms.

Typically, hypoglycemic onset is first evidenced by profuse perspiration, and subsequently by a decrease in skin temperature. Thus, decreased galvanic skin resistance, as a result of such perspiration, is typically the primary indicator in detection of hypoglycemic onset. However, diabetes tends to cause autonomic neuropathy, sometimes rendering a long-term diabetic incapable of perspiring (thereby degrading the reliability of perspiration as an indicator of hypoglycemic onset). Decreased temperature at the extremities, while typically occurring after the normal perspiration phase, tends to be a more reliable indicator of hypoglycemic onset, and is usually present in diabetics who lack the perspiration response.

In general, devices for measuring galvanic skin resistance are known. Typically, electrodes are disposed on the skin, and current passing between the electrodes is measured by a cooperating indicator device to provide indicia of the skin resistance. Typical indicator devices include analog meters calibrated in ohmic resistance, chart recorders, variable pitch or intensity sound sources, and lights.

Similarly, measurement of skin temperature is, in general, known. Skin temperature is typically sensed by a thermistor (temperature sensitive resistance) or similar device placed against the skin. Indicia of temperature is typically provided by a meter, variable tone source, or the like. In some cases a predetermined threshold or limit condition is established and an alarm sounded upon unfavorable comparison with such threshold condition.

Personal physiological monitors which generate an alarm indicia in response to changes in skin resistance, skin temperature, or both, are also known. An example of such a monitor is described in U.S. Pat. No. 4,178,916 issued to E. W. McNamara on Dec. 18, 1979. The McNamara device is adapted to be worn on the wrist of a diabetic. Skin resistance is sensed using respective electrodes disposed on the underside of the monitor casing the contact with the wearer's skin. A current is passed between the respective electrodes, and the voltage developed therebetween is compared to a fixed reference. In essence, an alarm indicia is generated when the skin resistance drops below a fixed predetermined value. Skin temperature is sensed utilizing a thermistor disposed on and projecting through the underside of monitor case to contact the wearer's skin. The thermistor is electrically connected in a bridge circuit with a manually set potentiometer. The potentiometer is typically set utilizing a thumbwheel. When the skin temperature drops below a threshold in accordance with the manually set potentiometer, alarm indicia are generated.

It is known that a monitor must generate alarm indicia capable of awakening even the deepest sleeper. However, space constraints inherent in a physiological monitor which can be worn on a human extremity impose limitations on the physical size of sound transducers which may be used, and on the size of any integral power supply available to the transducer. The McNamara patent proposes to solve such problem by radiating electromagnetic energy to a radio receiver in response to detection of an alarm condition. The radio would then generate a sound sufficiently loud to awaken a sleeper.

The prior art physiological monitors are disadvantageous in a number of respects. The constant current passed between the electrodes to sense skin resistivity constitutes a substantial power drain on the system, severely limiting the lifetime of battery cells in such monitor devices. Further, it has been found that the current flow between the respective terminals often causes skin irritation.

It has also been found that normal peripheral skin temperatures vary over a wide range of temperatures. Normal skin temperature not only varies from individual to individual, but also varies for a given individual under different ambient conditions. In addition, the "normal" peripheral temperature of a given individual varies during a period of approximately the first hour after the physiological monitor is first disposed on the wearer. It has been found that the monitor itself inhibits radiation heat loss from the skin area beneath the monitor, causing a gradual increase in the peripheral skin temperature under the monitor.

Further, it has been found that during sleep, peripheral blood flow (to the extremities) tends to decrease. As a result, while body core temperature does not change appreciably during sleep, the skin temperature at the extremities tends to vary, and is somewhat sensitive to ambient conditions. Accordingly, the skin temperature at, for example, the wrist, can vary as a function of the disposition of the arm, e.g. under the blankets, or exposed. Accordingly, as the ambient conditions of the extremity change due to changes in the sleeper's position, the monitoring device tends to be subject either to generation of frequent false alarms, or to the setting of an artificially low threshold temperature which requires an excessive decrease in skin temperature to generate alarm indicia. Such a situation is particularly dangerous for a diabetic incapable of perspiring due to autonomic neuropathy.

In addition, it has been found particularly difficult to manually set the temperature threshold potentiometer. As noted above, normal peripheral skin temperature varies over a wide range. The potentiometer, accordingly, must provide a range of resistances corresponding to the wide range of normal peripheral skin temperatures. The necessity of covering such a wide range of temperatures necessarily places constraints on the smallest increment of adjustment. Further, the potentiometer setting is subject to undesired changes due to accidental interaction of the adjustment thumbwheel with extrinsic objects.

SUMMARY OF THE INVENTION

The present invention provides a personal physiological monitor adapted to be conveniently worn on a human wrist which can reliably awaken a sleeper in the event of either a predetermined change in galvanic skin resistance or a predetermined change in peripheral skin temperature.

In accordance with one aspect of the present invention, power is conserved by briefly and periodically sensing skin resistance and/or skin temperature.

In accordance with another aspect of the present invention, a temperature reference is automatically established and alarm indicia is generated if the peripheral skin temperature drops a predetermined amount (e.g. 2° C.) below such value. The temperature reference is periodically corrected to accommodate slowly changing, non-symptomatic skin temperature variations.

In accordance with additional aspects of the present invention, particularly advantageous physical assembly is provided whereby skin irritation due to passage of current is minimized and any thermal interaction between the case and the thermistor is minimized. Further, alarm indicia sufficient to awaken even the deepest sleeper is provided without requiring external apparatus or power source, and without presenting an undue power drain on the monitor power source.

BRIEF DESCRIPTION OF THE DRAWING

A preferred exemplary embodiment of the present invention will hereinafter be described in conjunction with the appended drawing, wherein like designations denote like elements and:

FIG. 2 is a pictorial illustration of a monitor in accordance with the present invention disposed on the wrist of a wearer;

FIG. 3 is a pictorial representation of the underside of a monitor in accordance with the present invention;

FIG. 4 is a plan view of the interior of the monitor showing relative disposition of respective components of the monitor;

FIG. 5 is a sectional elevational view of the monitor of FIG. 4;

FIG. 5(A) is a detailed sectional elevational view of the coaxial element 68 shown in FIG. 5.

DETAILED DESCRIPTION OF A PREFERRED EXEMPLARY EMBODIMENT

Figure 1:
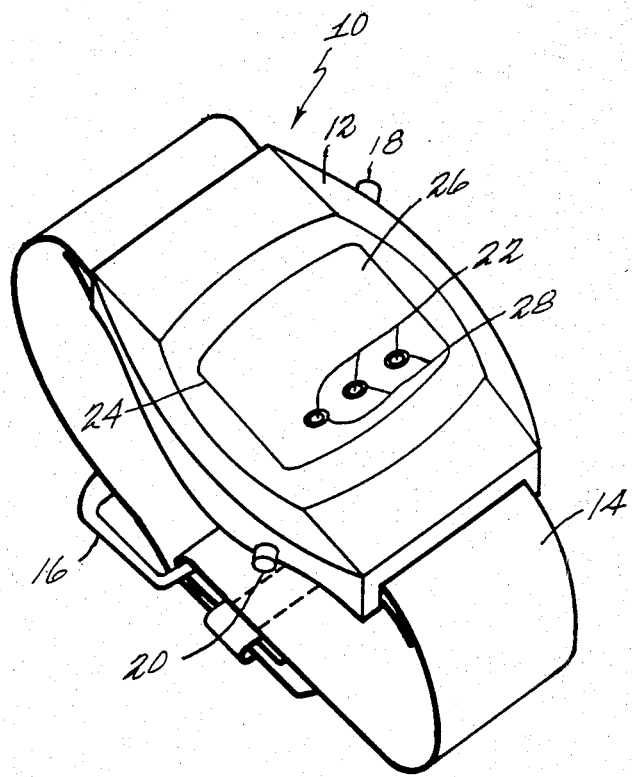
FIG. 1 is a pictorial representation of a personal physiological monitor in accordance with the present invention.

Referring now to FIG. 1, a personal physiological monitor 10 in accordance with the present invention comprises a case 12 fixed to a conventional wrist band 14. Case 12 is suitably formed of a rigid material such as metal or a plastic material. Wrist band 14 is fitted with a buckle 16. Respective control buttons 18 and 20 (employed to activate or deactivate the monitor 10, as will be explained) protrude from opposite sides of case 12. A plurality of sound port apertures 22, to be hereinafter more fully described, are formed in an outer face 24 of case 12. If desired, a decorative label 26 bearing suitable labeling (not shown) may be disposed on the face 24 of case 12.

As shown in FIG. 2, strap 14 is adapted to secure monitor 10 on the wrist of the wearer, with outer face 14 (containing sound port apertures 22) facing outwardly. The underside of case 12 (shown in FIG. 3) is maintained against the wearer's skin.

Referring now to FIG. 3, the underside of case 12 includes a removable case cover 30 formed of an electrically conductive material. Case cover 30 is secured, suitably by a friction fit, to the upper portion of case 12. An aperture 32, adapted to receive an annular insulating spacer 34 and an electrically and thermally conductive sensor cup 36, is centrally disposed in case cover 30. Case cover 30, insulating spacer 34 and sensor cup 36 are all maintained in contact with the wearer's skin by strap 14. Insulating spacer 34 provides both electrical and thermal insulation between cover 30 and sensor cup 36. As will hereinafter be explained, sensor cup 36 is adapted to receive a temperature sensitive element such as a thermistor and maintain the thermistor in thermal contact with the wearer's skin. The relationship of case cover 30, insulating spacer 34, sensor cup 36, and the temperature sensitive element, will be more fully described in conjunction with FIG. 5.

Referring now to FIGS. 4 and 5, monitor 10 includes, contained within case 12: electronic circuitry 40, in the form of an integrated circuit (IC); a crystal 42; a sound transducer 44; a tantalum chip capacitor 46; a ceramic capacitor 45; a resistor 98; and a power source (battery) 48. The spatial disposition of the respective components within case 12 is shown schematically in FIG. 4 in plan view. The respective components are maintained on a printed circuit (PC) board 50, in cooperation with a thermoplastic mounting block 52 (FIG. 5). Thermoplastic mounting block 52 is secured to PC board 50 by respective heat formed protrusions 52a (FIG. 5) integral to block 52. Protrusions 52a are snap fit in corresponding apertures 53 in PC board 50. PC board 50 is, in turn, secured to the upper portion of case 12, suitably by screws 51. Electrical connections between PC board 50 and cover 30 are also effected by means of the screws 51.

Control buttons 18 and 20 are mounted in and extend through opposite sidewalls of case 12. Respective compression springs 18a and 20a are disposed about push button 18 and 20 to provide outward force. Push buttons 18 and 20 cooperate with respective resilient conductive switch arms 18b and 20b and fixed contacts 18c and 20c, mounted and electrically connected to printed circuit board 50. Inward radial pressure applied to buttons 18, 20 causes the buttons to contact and flex their respective associated switch arms 18b, 20b, ultimately establishing electrical contact between the switch arms and the associated fixed contacts 18c, 20c.

Electronic circuitry 40 suitably comprises an integrated circut housed in a ceramic leadless chip carrier and is attached to printed circuit board 50 by soldering the respective terminals to corresponding pads on PC board 50. Electronic circuitry 40 will hereinafter be described in greater detail in conjunction with FIG. 6. Crystal 42 suitably comprises a Statek type WX-7V32.768 crystal (of the type utilized in digital watches).

Power for monitor 10 is provided by battery 48. Referring now to both FIGS. 4 and 5, battery 48 suitably comprises two mercuric oxide cells 48a, ANSI designation M11, providing a total battery voltage of 2.8 volts. The average service capacity in such cells, as stated by the manufacturer, is 160 Ma-hours. Battery 48 is disposed within a cavity 48b in thermoplastic mounting block 52 and is maintained in electrical contact with a conductive pad 50a on PC board 50 by a battery contact spring 54. Battery contact spring 54 is suitably formed of thin corrosion-resistant spring material and also provides for a negative electrical contact between a battery 48 and PC board 50 (contact not shown). Capacitor 46 (e.g. 33 uf) is connected, through conductors (not shown) on PC board 50, in parallel with battery 48.

Transducer 44 comprises an axially-polarized ferrite ring magnet 44a, a magnetically-soft iron pole piece 44b, a copper coil 44c, a magnetic diaphragm 44d, and a diaphragm weight 44e. Ring magnet 44a and pole piece 44b are mounted on PC board 50, with pole piece 44b concentrically disposed within ring magnet 44a. Coil 44c is wound about pole piece 44b. Diaphragm 44d is mounted on ring magnet 44a overlying pole piece 44b, with weight 44e centrally disposed thereon.

Transducer 44 may be provided from components from a commercially available "transducer" such as the Star Micronics Model QMB-111 miniature audio transducer. The Star Micronics transducer includes a transducer assembly disposed within a resonator cap. The cap may be removed and the transducer assembly utilized as transducer 44. Transducer 44 is disposed within a cylindrical bore 57 (FIG. 5) formed in thermoplastic block 52. Bore 57 communicates with a lesser diameter bore 56. Bore 56 is disposed concentric with bore 57, overlying diaphragm 44d. A depression 58 is formed in the interior surface of face 24 of case 12, in registry with bore 56. Sound port apertures 22 communicates between depression 58 and the exterior of the case. Bore 56, depression 58 and apertures 22 cooperate to form a Helmholtz resonator for transducer 44, tuned to the second harmonic of the transducer fundamental frequency. Bore 56 and depression 58 form a cavity 60, which presents a predetermined volume of air to transducer diaphragm 44d. The total (combined) cross section and length of sound port apertures 22 are chosen in predetermined relation to the volume of cavity 60. Cavity 60 and sound port apertures 22 thus cooperate to form a Helmholtz type resonator 61. The natural resonant frequency of transducer 44 is suitably 2048 Hz. The Helmsholtz resonator, is, in turn, dimensioned to generate a strong component of the second harmonic (4096 Hz) of the natural transducer frequency.

It has been found that older people often tend to be incapable of hearing sound having frequencies in certain frequency ranges, e.g. about 3,000 Hz. However, transducer 44 and resonator 61 cooperate to generate sounds having frequency components in various ranges so that the sound is discernable by people having different classes of hearing loss. In addition, the frequency composition, i.e. high second harmonic content of the sound, is chosen to be extremely piercing, strident, and discordant to ensure that a sleeper is awakened. In addition, as will hereinafter be explained, the time sequence of "beeps" is specifically chosen to be unsymmetrical or irregular to further enhance the alerting nature of the alarm.

As previously noted, cover 30 is secured to the underside of case 12. A lip 62 is provided about the periphery of the underside of case 12. A friction fit is provided between inner cover rim 30a and lip 62. Cover 30, spacer 34, and cup 36 are formed as a single assembly. Cup 36 includes a peripheral rim 36a formed in a side wall thereof. Cup 30 similarly includes a depressed rim 30b about the central aperture. Spacer 34 is formed of an electrically and thermally insulative thermoplastic material, and is adapted to interlock with cup rim 36a and the depressed inner rim 30b of cover 30. Cover 30 and cup 36 are suitably fabricated from corrosion resistant metal and are insulated, both electrically and thermally, from each other by thermoplastic spacer 34.

A temperature sensitive device 64 is mounted in cup 36. Temperature sensitive device 64 is suitably a Fenwall Electronics JT45J5 thermistor, having a resistance of approximately 34kΩ at 33° C. and a negative temperature coefficient of approximately −4.7% per degree C. Thermistor 64 is suitably fixed to cup 36 by an electrically conductive adhesive 66. Electrical connections between cup 36, thermistor 64 and PC board 50 are provided utilizing a cylindrical coaxial element 68 formed of resilient thermally insulative material. Coaxial element 68 (shown broken out in FIG. 5a) is formed of a conductive silicone rubber core 68a, a concentric non-conductive silicone rubber intermediate sleeve 68b, and a concentric conductive silicone rubber outer sleeve 68c. Intermediate sleeve 68b is interposed between and isolates conductive core 68a and conductive outer sleeve 68c. The diameter of core 68a is chosen to be less than the diameter of thermistor 64, whereas the outer diameter of insulative intermediate sleeve 68b is greater than the diameter of thermistor 64. A conductive pad 50h, and annular conductive ring 50j, are disposed in registry with core 68a and outer sleeve 68c, respectively, on the underside of PC board 50. Accordingly, an electrical circuit connection is established from conductive pad 50h through core 68a, to thermistor 64 and from thermistor 64 through cup 36 and outer sleeve 68c to conductive ring 50j.

Resilient coaxial conductor 68 provides constant pressure against the interconnected elements, and thus maintains reliable electrical connections. In addition, since coaxial element 68 is relatively thermally insulative, thermistor 64 is thermally isolated from case 12 and is therefore not subject to heat "sinking" by case 12.

Figure 6:
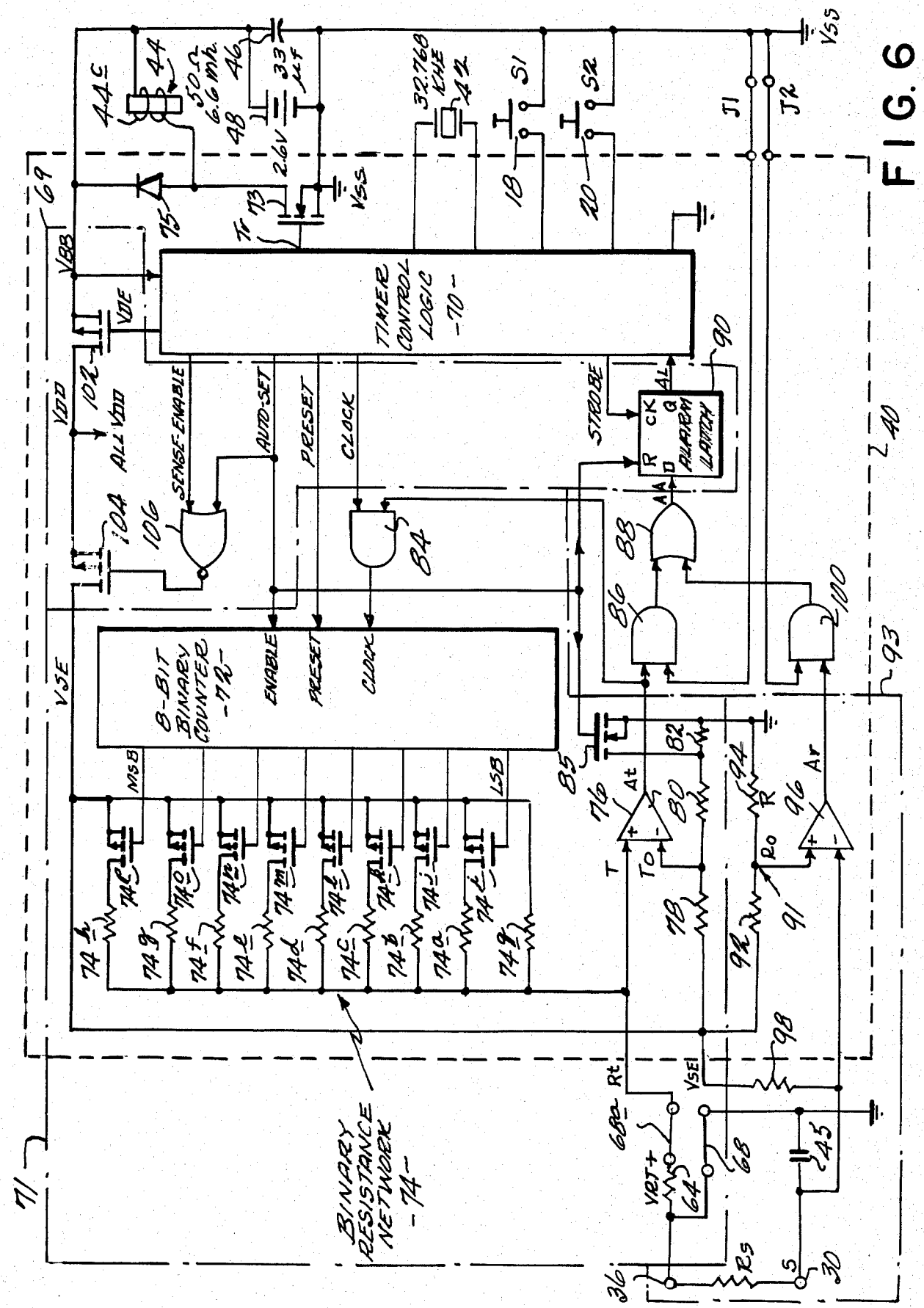
FIG. 6 is a schematic diagram of the electrical circuitry associated with the present invention.

Circuitry (IC) 40 provides, in cooperation with thermistor 64, cap 36 and cover 30, the skin temperature sensing and skin resistance sensing functions of monitor 10, and generates appropriate signals to transducers 44 to effect respective alarm indicia. Referring now to FIG. 6, IC 40 suitably includes suitable timer/control logic circuitry 70 for generating a predetermined timed sequence of respective control signals to effect a programmed operation of monitor 10, cooperating with suitable power conservation circuitry 69, a suitable temperature sensing system 71, a suitable skin resistance sensing system 93, and circuitry for selectively activating transducer 44.

Control logic 70 is utilized to generate respective control signals: $V_{de}$, Preset, Autoset (A-S), Sense Enable (SE), Strobe, $T_r$ and a clock signal (CK). Briefly, control signal $V_{de}$ is utilized, in conjunction with power conservation circuitry 69, for controlling application of power to portions of monitor 10 other than control logic 70. The Sense Enable and Strobe control signals are similarly utilized in conjunction with power conservation circuitry 69, to generate a limited duty cycle power signal ($V_{se}$) for application to the primary power consumption portions of the circuit and to provide for synchronous sampling of alarm conditions. The Preset and Autoset control signals and the clock signal are used in conjunction with temperature sensing system 71 for establishing indicia of a temperature reference, thereby compensating for non-symptomatic skin temperature variation.

Figure 7:
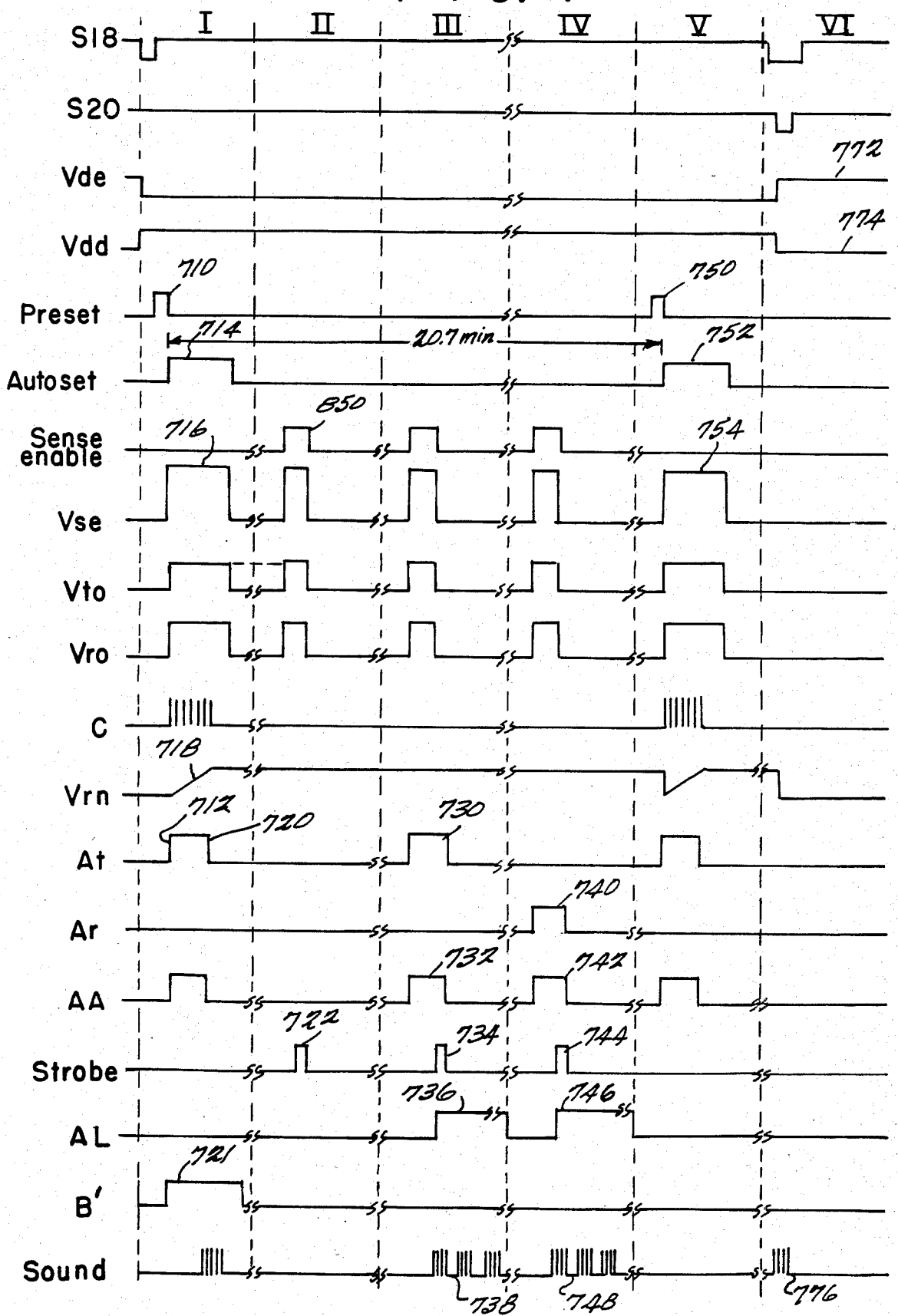
FIG. 7 is a timing and waveform diagram of various signals associated with a monitor in accordance with the present invention.
Figure 8:
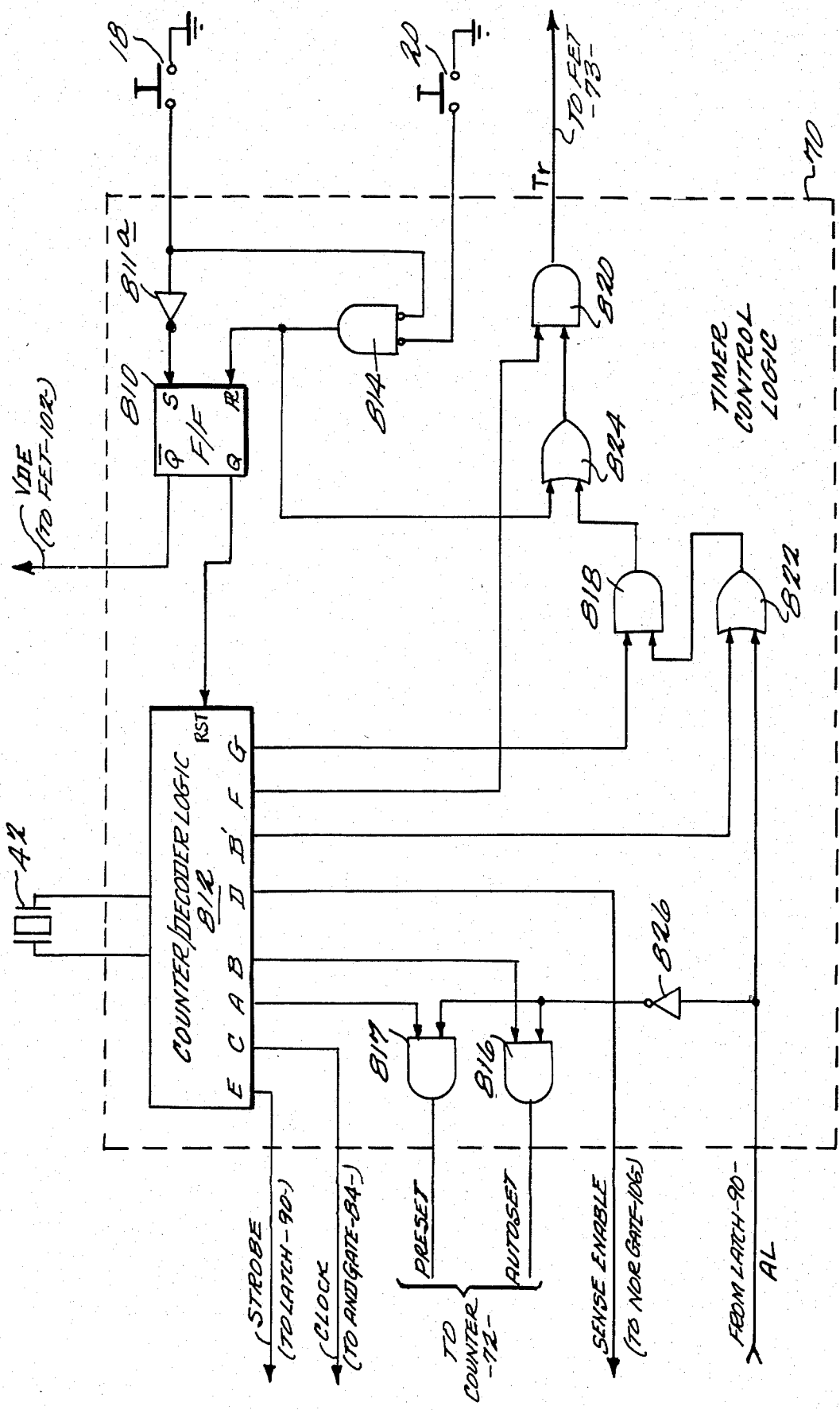
FIG. 8 is a block schematic of a suitable timer/control logic shown in FIG. 6.

With reference now to FIGS. 7 and 8, control logic 70 suitably comprises a conventional RS flip flop 810, suitable conventional counter/decoder logic 812, and respective AND gates 816, 817, 818 and 820, OR gates 822 and 824 and gate 814 and inverters 811a and 826. Counter/decoder logic 812 suitably generates, in a conventional manner, respective output signals:

(812A) A sequence of pulses 1 ms in duration, at intervals of 1,250 seconds, i.e. approximately 20.8 minutes;

(812B) 391 ms-long pulses repeated at intervals of 1,250 seconds, initiated immediately after each 1 ms pulse at output 812A;

(812B') A single 391 ms pulse corresponding to the first pulse of the signal of output 812B;

(812C) A 1024 Hz square wave;

(812D) A app. 7.8 ms pulse repeated at intervals of approximately 4.9 seconds;

(812E) A 1.9 ms pulse repeated at intervals of approximately 4.9 seconds, in synchronism with but delayed 5.9 ms from the onset of the 7.8 ms pulse of output D;

(812F) A sequence of 319 ms groups of 2048 Hz square waves, repeated at intervals of 977 ms; and (812G) A sequence of 39.1 ms pulses repeated at intervals of 97.7 ms.

The $V_{de}$ signal is provided at the Q output of flip flop (F-F) 810. The set (S) input of F-F 810 is coupled (through an inverter 811a) to switch 18. Closure of switch 18 generates a negative going pulse S1 which is inverted and applied to the S input, causing the $\overline{Q}$ output of F-F 810, $V_{de}$, to assume a low level value. The reset (R) input of F-F 810 is receptive of the output signals from two input NAND gate 814. The input terminals of NAND gate 814 are coupled to switches 18 and 20. Thus, when the switches 18 and 20 are concurrently depressed, F-F 810 is reset and the $\overline{Q}$ output thereof, $V_{de}$, goes high. In practice, provisions to inhibit pulse action may be incorporated into the logic circuitry.

The Sense Enable (SE) and Strobe signals are provided at outputs D and E of counter/decoder logic 812 of control logic 70. Thus, the Sense Enable signal (SE) comprises 7.8 ms pulses occurring at 4.9 seconds intervals and the Strobe signal comprises synchronous 1.9 ms pulses occurring 5.9 ms after the onset of the Sense Enable pulses, as illustrated in FIG. 7.

The Preset (P) and Autoset (A-S) signals are generated by gating the 812A and 812B outputs of counter/decoder 812, respectively, with a signal indicative of the absence of an alarm condition, through two input AND gates 816 and 817. Thus, the Preset and Autoset signals comprise synchronous 1 ms and 391 ms pulses, respectively, occurring at 1250 second intervals with the 391 ms Autoset pulses immediately succeeding the corresponding Preset pulses.

Control signal $T_r$ is utilized to effect controlled operation of transducer 44, and comprises three different characteristic forms in accordance with the various operational modes of monitor 10, as will be explained. Referring to FIG. 6, the activation of transducer 44 is effected by application of the $T_r$ control signal from control logic 70 to the gate of an N channel FET 73. FET 73 selectively completes a current path through coil 44c of transducer 44 to generate audio indicia. A diode 75 is connected in parallel with coil 44c to suppress back EMF transient voltages.

Power conservation circuitry 69 is utilized to minimize the power drain on battery 48, and thus extend the life of the battery. Control logic 70 is preferably formed of low power CMOS devices. Accordingly, a direct connection (shown in FIG. 6, not shown in FIG. 8) to battery 48 (such that power is continuously applied to control logic 70) is provided without substantial power drain on battery 48. However, the remainder of the circuitry and, in particular, respective resistive voltage divider networks within temperature sensing system 71 and resistance sensing system 93 can consume relatively substantial amounts of power.

Accordingly, battery 48 is selectively coupled to the remainder of the circuitry of monitor 10 circuitry through a P channel FET 102, controllably rendered conductive by application of a negative gate control voltage $V_{de}$ from control logic 70.

Referring briefly to FIGS. 6, 7 and 8, general application of power to the components of monitor 10 is initiated by momentary closure of switch 18. Closure of switch 18 sets RS flip flop 810 (FIG. 8) in control logic 70. The $\overline{Q}$ output of flip flop 810, accordingly assumes a low level value. The low level $\overline{Q}$ output of flip flop 810 is applied as signal $V_{de}$ to the gate of P channel FET 102 and the output of FET 102, $V_{dd}$ accordingly becomes equal to the battery voltage, $V_{bb}$ (e.g. 2.8 volts).

To further conserve power consumption, current is provided to sensing systems 71 and 93 on a periodic basis, established by the Sense Enable (SE) control signal.

Referring again to FIG. 6, the output $V_{dd}$ of FET 102 is applied to sensing systems 71 and 93 through another P channel FET 104. FET 104 is rendered conductive only when at least one of the Sense Enable or Autoset control signals from control logic 70 is at a high level. The Sense Enable and Autoset signals are applied to the respective inputs of a conventional two input NOR gate 106. The output of NOR gate 106 is applied to the gate of FET 104. The Autoset and Sense Enable signals are periodic with relatively low duty cycles (e.g. 7.8 ms each 4.9 seconds). Thus, FET 104 is rendered conductive only periodically, and a periodic limited duty cycle power signal, hereinafter referred to as $V_{se}$, is provided at the drain of FET 104 for application to sensing systems 71 and 93. The major power consuming elements of circuit 40 are thus only periodically energized and power consumption is reduced.

Temperature sensing system 71, in effect, generates appropriate signals to initiate an alarm when the skin temperature decreases by a predetermined amount (e.g. 2° C.), indicative of an alarm condition. A temperature reference is initially established, and is suitably periodically updated to compensate for slowly changing, non-symptomatic skin temperature variations. Temperature sensing system 71 comprises a conventional 8-bit binary counter 72, a variable resistance network 74, a variable reference voltage divider 77, a conventional comparator 76, and a two input AND gate 84.

The Autoset and Preset control signals and clock signal 812C (CK) from control logic 70 are applied to temperature sensing system 71 to effect storing indicia of the reference temperature. The Autoset and Preset control signals are applied to the enable and preset control terminals, respectively, of binary counter 72. In some instances, for example, where the enable circuitry of counter 72 is level sensitive and the preset circuitry is transition sensitive, the Autoset signal may operate as both enable and preset control signals to counter 72, and a separate preset signal from logic 70 can be dispensed with. The output terminals of counter 72 are connected to the respective elements of variable resistance network 74.

Resistance network 74 is, in effect, a multiplying digital to analog converter which provides a current output in accordance with the contents of counter 72 and the voltage $V_{se}$. Resistance network 74 suitably includes a plurality of resistors (74a–74h) and serially connected switching devices associated with each bit of counter 72, e.g. eight resistors of differing values 6.4MΩ, 3.2MΩ, 1.6MΩ, 800kΩ, 400kΩ, 200kΩ, 100kΩ, and 50kΩ, each connected in series with a P channel (74i–74p). The gate of each FET is coupled to the associated output of counter 72. The series combinations are, in turn, connected in parallel, together with an unswitched resistor 74q (e.g. value 74kΩ), between the respective terminals of the network.

The FETS 74i–74p are selectively rendered conductive or non-conductive in accordance with the state of the associated counter bit as counter 72 is incremented, to selectively connect and disconnect the respective resistances from the parallel resistance network. Where P-channel FET's are used, the equivalent resistance of network 74 increases in a discrete manner (256 steps) from a minimum value (all resistances in parallel, e.g. 18.8kΩ) when binary counter 72 is in all zero state, to a maximum value (the resistance of the non-switched resistor, e.g. 74kΩ). The values of the individual component resistors are chosen in accordance with the resistance characteristics of thermistor 64, as will be explained.

Network 74 forms a voltage divider network with thermistor 64. Resistive network 74 is connected at one terminal to the drain of FET 104. The other terminal of resistive network 74 is connected to thermistor 64 through PC board 50 and conductive core 68a of resilient element 68. Thermistor 64 is, in turn, coupled through cap 36, conductive outer sleeve 68c of resilient element 68, and PC board 50, to the system ground ($V_{ss}$). Thus, resistive network 74 and thermistor 64 are serially connected between $V_{se}$ and ground potential $V_{ss}$, and operate as a voltage divider network with respect to the signal $V_{se}$. The voltage, $V_{Rt}$, dropped across thermistor 64 is therefore equal to $(R_t/(R_t+R_N))(V_{se})$, where $R_t$ is the resistance of thermistor 64 and $R_N$ is the equivalent resistance of network 74.

The voltage across thermistor 64, $V_{Rt}$, is applied to the non-inverting input T of comparator 76. The input signal to the inverting input $T_o$ of comparator 76 is provided by variable reference voltage divider 77. Reference voltage divider 77 is formed of respective resistances 78, 80 and 82 serially connected between $V_{se}$ and system ground potential $V_{ss}$ and an n-channel FET 85 connected across resistor 82. The voltage drop across resistors 80 and 82 is provided as the input to inverting input terminal $T_o$ of comparator 76.

FET 85 selectively couples resistor 82 into and out of the reference voltage divider. The Autoset signal from control logic 70 is applied as a control signal to the gate of FET 85 to render FET 85 conductive and effectively remove resistor 82 from the voltage divider, for the duration of the Autoset pulse. The respective values of resistors 78, 80 and 82 (e.g. 200kΩ, 182.5kΩ and 17.5kΩ, respectively) are chosen so that the voltage applied to inverting terminal $T_o$ is equal to a proportion of $V_{se}$ less than $0.500V_{se}$ (e.g. $0.477V_{se}$) during the Autoset period when resistor 82 is operatively removed from voltage divider 77, and a greater proportion (e.g. $0.500V_{se}$) when resistor is operative in voltage divider 75. The proportion differential associated with the removal of resistor 82 corresponds to the proportion differential in $V_{Rt}$ due to the predetermined drop in skin temperature (e.g. 2° C.) chosen as an alarm condition. The output $A_t$ of comparator 76 is utilized to selectively enable AND gate 84 to pass clock pulses from control logic 70 so long as the proportion of $V_{se}$ dropped across thermistor 64 is greater than the reference proportion of Vse established by the reference voltage divider, i.e. $0.477V_{se}$ during the Autoset period. The output $A_t$ of comparator 76 is applied to one input terminal of two input AND gate 84. The other input of AND gate 84 is receptive of the 1024 Hz clock signal from control logic 70. The output of AND gate 84 is applied to the clock input C of counter 72.

The output $A_t$ of comparator 76 is also applied to one input terminal of another two input AND gate 86. The output of AND gate 86 is applied through a two input OR gate 88 to the D input of D type flip flop 90 (hereinafter sometimes referred to as alarm latch 90). The second input of AND gate 86 is maintained high by a pull-up resistor (not shown), but is adapted for connection to system ground $V_{ss}$ by a jumper J1 in the event that it is desired to inhibit generation of an alarm in response to temperature sensing.

Alarm latch 90 is utilized to provide for a sampling of alarm conditions synchronous with application of power to sensing systems 71 and 93, as will be explained. Latch 90 is periodically clocked by the Strobe signal from control logic 70 and the Q output A1 of latch 90 is applied to control logic 70 to selectively effect generation of alarm indicia, as will also be explained.

Referring now to FIGS. 6 and 7, temperature sensing system 71 in response to the Preset and Autoset signals from control logic 70 establishes a count corresponding to the instantaneous skin temperature sensed by thermistor 64. Application of the preset signal 710 to counter 72 presets counter 72 to a predetermined count (suitably an all zero state) corresponding to a chosen equivalent network resistance $R_N$ (suitably the minimum value 18.8KΩ). The preset value is chosen to correspond to a predetermined value considerably less than the thermistor resistance $R_t$ at typical skin temperatures. Accordingly, when $V_{se}$ assumes a non-zero value in response to the Autoset pulse, the voltage dropped across resistive network 74 is relatively low and more than half of $V_{se}$ is dropped across thermistor 64. Accordingly, $V_{Rt}$ is initially significantly greater than $0.477V_{se}$.

Immediately upon termination of the Preset signal 710, a 391 ms Autoset pulse 714 is generated. The Autoset signal performs a number of functions. As previously mentioned, the Autoset signal is applied through NOR gate 106 to render FET 104 conductive, such that $V_{se}$ is equal to the battery voltage $V_{bb}$ (i.e. power is applied to sensing systems 71 and 93) for the duration of the Autoset period. The Autoset signal is also applied to the gate of FET 85, rendering FET 85 conductive and effectively removing 17.5kΩ resistor 82 from the reference voltage divider 77. The reference voltage divider 77 thus effectively consists of 200kΩ resistor 78 serially connected with 182.5kΩ resistor 80, with the voltage drop across resistor 80 being applied to the inverting input terminal $T_o$ of comparator 76. Accordingly, the voltage at the inverting input $T_o$ of comparator 76 is equal to $0.477V_{se}$.

As noted above, the preset value of equivalent network resistance $R_N$ of network 74 is chosen such that the voltage $V_{Rt}$ at the non-inverting input T of comparator 76 is considerably greater than $0.477V_{se}$. Accordingly, upon occurrence of the Autoset pulse, causing $V_{se}$ to take a non-zero value, the output $A_t$ of comparator 76 will go high (pulse 712), enabling AND gate 84 with respect to clock signals from control logic 70. It is noted that a high level output signal $A_t$ from comparator 76 would tend to initiate generation of an alarm through latch 90. However, the Autoset signal is also applied to the reset terminal of latch 90, to hold the Q output of latch 90 at a low level for the duration of the Autoset period, and thus inhibit generation of an alarm signal.

In addition, the Autoset signal is applied to the enable terminal of counter 72. Counter 72 is thus enabled with respect to the clock signals provided through AND gate 84 and begins to accumulate a count.

As the accumulated count in counter 72 is incremented by the clock signal (CK), the equivalent resistance $R_N$ of network 74 increases, causing the voltage drop $V_{Rn}$ across network 74 to increase. The proportion voltage drop $V_{Rt}$ across thermistor 64 thus decreases concomitantly. Ultimately, a count is attained such that the voltage drop $V_{Rt}$ across thermistor 64 is slightly less than 0.477 of $V_{se}$. At this point, the output $A_x$ of comparator 76 will go low (falling edge 720 shown in FIG. 7), inhibiting AND gate 84 and preventing application of further clock pulses to counter 72.

Thus, a count comprising indicia of the instantaneous skin temperature sensed by thermistor 64 is established in counter 72 and the predetermined lower reference potential $(0.477V_{se})$ is, in effect, equated to the instantaneous temperature.

At the end of the Autoset period, counter 72 is disabled with respect to any clock signals thereafter applied (until the next Autoset period). The count accumulated in counter 72 is therefore maintained (stored) in the counter until the next Autoset period and is utilized as the temperature reference.

To assure that an equivalent network resistance $R_N$ corresponding to the $0.477V_{se}$ reference level is attained within the Autoset period, the duration of the Autoset pulses 714 (391 ms) is relatively long and the frequency (1024 Hz) of the clock signal is relatively high. Preferably, the duration of the Autoset period is sufficiently long and clock frequency sufficiently high to permit counter 72 to be incremented through its entire range of operation, i.e. 255 clock pulses, during the Autoset period.

It is desirable that an audible indication that the Autoset function has been completed be provided to the wearer. Accordingly, with reference to FIG. 8, the B' output of counter/decoder logic 812 (corresponding to the first Autoset pulse) is applied through OR gate 822 to enable AND gate 818 with respect to the sequence of 39.1 ms pulses (at 97.7 ms intervals) provided at output 812G of counter/decoder logic 812. The 39.1 ms signals 721 (FIG. 7) are applied through OR gate 824 to one input of AND gate 820, to enable AND gate 820 with respect to the 391 ms groups of 2048 Hz square waves (at intervals of 977 ms) provided at output F of logic 812. The output of AND gate 20 is applied as the control signal $T_r$ to FET 73. Accordingly, during the course of the first 391 ms Autoset period, FET 73 is selectively rendered conductive to provide a current path through coil 44c of transducer 44 to generate four short beeps, (39.1 ms bursts of 2048 Hz and harmonics) characteristic of the Autoset function.

In the subsequent description of skin temperature and resistance sensing, the active 7.8 ms sense enable interval is assumed, and the Vse voltage is momentarily at the Vdd level (i.e. 2.8 volts).

At the end of the Autoset period, after the indicia of the reference temperature is established in counter 72, the reference voltage to the inverting input of comparator 76 is adjusted to correspond to a temperature a predetermined number of degrees (e.g. 2° C.) less than the reference temperature. At the end of the Autoset pulse, FET 85 is rendered non-conductive, such that the 17.5kΩ resistor 82 operatively becomes part of reference voltage divider 77. The voltage applied to the non-inverting input terminal $T_o$ of comparator 76 thus becomes equal to $0.500V_{se}$, corresponding to a temperature 2° lower than that reflected by the count in binary counter 72. Thus, if the skin temperature thereafter decreases by more than 2° (causing a concomitant increase in the resistance of thermistor 64), the voltage drop $V_{Rt}$ across thermistor 64 will increase to a level greater than $0.500V_{se}$, causing output $A_t$ from comparator 76 to produce a positive output 730 for application through gates 86 and 88 to the D input of alarm latch 90. Latch 90 responsively causes generation of alarm indicia, as will be explained.

It should be noted that the high level output 730 of signal $A_t$ from comparator 76 also enables AND gate 84 with respect to the clock pulses provided by control logic 70. However, since no Autoset signal is present to enable counter 72, the count stored in counter 72 is undisturbed.

As previously mentioned, in order to compensate for relatively slow non-symptomatic temperature variations, the Autoset signal is periodically regenerated, e.g. at 20.8 minute intervals. If desired, timer control logic 70 can be structured to cause the Autoset intervals to occur more frequently during the first hour of wear, and thereafter reoccur at longer time intervals.

The possibility of the onset of a hypoglycemic episode just prior to or during an Autoset period has been considered. The generation of Autoset signals are inhibited during periods where an alarm condition exists. Referring to FIG. 8, the signal Al from latch 90, indicative of an alarm condition, is applied through an inverter 826 to AND gates 816 and 817 to gate the 1 ms and 391 ms pulses from output terminals A and B of counter/decoder logic 812. Thus, when signal AL is high, signifying the existence of an alarm condition, the output of inverter 826 is low, inhibiting gates 816 and 817 and thus preventing application of the Preset and Autoset pulses to temperature sensing system 71.

It is possible, however, for an Autoset period to occur just prior to an alarm condition. For example, an Autoset period can occur after the skin temperature has already decreased a substantial amount (but less than the 2° temperature decrease threshold). The Autoset period would thus establish new lower skin temperature reference and an alarm would not be sounded until the temperature decreases an additional two degrees from the new reference temperature.

The probability of such a time relationship between a hypoglycemic episode and an autoset period is highly unlikely. Moreover, in most instances, the hypoglycemic episode will be evidenced by profuse perspiration, and an alarm would therefore be effected by resistance sensing network 93.

Skin resistance sensing system 93, in effect, generates appropriate signals to initiate an alarm when skin resistance drops below a predetermined value, indicative of profuse perspiration. Skin resistance sensing system 93 basically comprises a reference voltage divider 91, anode (cover 30) and cathode (cap 36) terminals, a comparator 96 and a resistor 98. More specifically, reference voltage divider 91 comprises respective resistors 92 and 94 serially connected between the drain of FET 104 ($V_{se}$) and ground potential $V_{ss}$. Resistors 92 and 94 are suitably of the same value (e.g. 200k$\Omega$), and provide at the juncture therebetween a reference signal, $R_o$ (equal to $0.500V_{se}$) to the non-inverting input terminal of a comparator 96. The skin resistance $R_s$ is interjected into the system between anode (cover) 30 and cathode (cap) 36. Resistor 98 is, in effect, connected in series with the skin resistance $R_s$ between the drain of FET 104 and system ground. More particularly, one terminal of resistor 98 (external to IC 40) is connected (in part by conductors of PC board 50) to the drain of FET 104. The other terminal thereof is connected via conductors on PC board 50 to case cover (anode) 30. As previously noted, isolated conductive cup (cathode) 36 is connected through conductive outer core 68c to system ground potential $V_{ss}$. Accordingly, a current path is established from voltage $V_{se}$ through resistor 98, to cover 30, then through the galvanic skin resistance $R_s$ to ground. The voltage drop across skin resistance $R_s$ is applied to (i.e. the juncture between resistor 98 and cover 30 is connected to) the inverting input of comparator 96. Accordingly, the output of comparator 96 goes high when the voltage drop across salveric skin resistance $R_s$ drops below the reference voltage ($0.500V_{se}$) established by reference voltage divider 91. In addition, 0.01uf capacitor 45 is connected between cover 30 and ground potential. The values of resistors 92 and 94 are chosen to provide a predetermined proportion (0.500) of voltage $V_{se}$ to comparator 96 as a reference.

The output $A_r$ of comparator 96 is applied to one input terminal of a two input AND gate 100, the output of which is applied to an OR gate 88 the output of OR gate 88 is converted to the D input of latch 90. In a manner similar to AND gate 86, the second input of AND gate 100 is maintained high, but is adapted for connection to system ground through a jumper J2 in the event that it is desired to inhibit generation of alarms in response to changes in skin resistance.

The value of resistor 98 is chosen in accordance with the desired threshold value of skin resistance. Where, as in the preferred embodiment, the reference voltage applied to the non-inverting input terminal of comparator 96 is equal to $0.500V_{se}$, resistor 98 is chosen to have a value equal to the predetermined threshold skin resistance. Empirical studies have shown that the galvanic skin resistance in the presence of profuse perspiration is significantly less than 200k$\Omega$. Accordingly, a threshold value of 200k$\Omega$ has been chosen (i.e. resistor 98 has a value of 200k$\Omega$). Clinical testing has proven the 200k$\Omega$ threshold value to be satisfactory.

Resistor 98 is disposed external to IC 40 in order to ensure high precision. While it is relatively easy to provide high ratiometric accuracy in respect of resistors formed internal to an integrated circuit, it has proven difficult to provide highly precise absolute values of resistance. Accordingly, resistor 98 is disposed external IC 40 to provide more accurate control of the skin resistance threshold value, as well as to facilitate changing the predetermined threshold resistance if subsequently required. A variable resistance can, of course, be utilized if desired.

In operation, when no perspiration is present on the skin, the value of galvanic skin resistance $R_s$ is considerably higher than the 200k$\Omega$ threshold value. Accordingly, more than $0.500V_{se}$ is dropped across the skin resistance $R_s$. The input to the non-inverting terminal of comparator 96 is thus greater than that applied to the non-inverting input and, accordingly, the output, $A_r$, of comparator 96 is at a low level. However, when perspiration is present on the skin, the galvanic skin resistance decreases to below on the order of 200k. Accordingly, less than $0.500V_{se}$ is dropped across the skin resistance. The reference voltage applied to the non-inverting input of comparator 96 thus becomes greater than that applied to the inverting input and the output $A_r$ goes high. The high level $A_r$ signal is applied through AND gate 100 and OR gate 88 to the D input of alarm latch 90. Latch 90, in turn, generates an alarm signal AL to control logic 70 to effect generation of alarm indicia as will be explained.

It has been found that provisions to protect circuitry 40 from large electrostatic voltages which may be present in the wearer's body are desirable. For example, the wearer's body represents a capacitance of on the order of 200 pf and typically can carry an electrostatic charge of on the order of a few thousand volts. If the high voltage electrostatic charge is discharged into circuitry 40, serious damage can result. Such a discharge can occur in the unlikely event that the wearer comes into contact with cap 36 prior to coming into contact with any other conductive portion of case 12. Accordingly, as previously noted, an 0.01 $\mu$f capacitor 45 is connected in parallel with the skin resistance sensing terminal S, i.e. is connected between cover 30 and cap 36 or ground potential. Capacitor 45, in effect, operates as a capacitive voltage divider with the wearer's body capacitance, reducing the effective capacitance viewed by circuit 40 by a factor of on the order of 50. The electrostatic voltage discharge into circuitry 40 is thereby reduced to on the order of 100 volts, which is well within the effective range of conventional internal protection devices (not shown) which may be built into IC 40.

As previously noted, many people using the prior art skin resistance sensors experienced skin irritation. Even though the current passing through the skin was typically less than 10 microamperes, it contributed to skin irritation. In addition, it was found that low order electro-plating and consequent corrosion tended to occur at the anode electrode (more positive electrode). Monitor 10 has essentially eliminated such skin irritation and corrosion. By supplying current through the sensing system only intermittently, the average current through the skin is considerably reduced. In addition to conserving power, the reduced average current has been found to reduce skin irritation. In addition, the configuration of electrodes (in particular the use of the relatively large surface area of cover 30 as the anode terminal) significantly reduces the current density and also has been found to reduce skin irritation.

As previously noted, generation of an intermittent current to sensing systems 71 and 93 and synchronous sampling of alarm conditions is effected by power conservation circuitry 69. With reference to FIG. 6, power is provided to sensing circuitry continuously during Autoset periods, by application of the Autoset pulses to NOR gate 106 as previously explained. However, when the high level Autoset pulse is removed from NOR gate 106, FET 104 is rendered non-conductive, and $V_{se}$ assumes a zero value.

Thereafter $V_{se}$ assumes a positive value only in response to the respective Sense Enable pulses 850 provided by timer control logic 70. As previously noted, the sense enable pulses 800 are 7.8 ms in duration, and are repeated at intervals of approximately 4.9 seconds (presenting a duty cycle of only about 0.15%). Accordingly, the average current supplied to (and thus energy consumed by) sensing systems 71 and 93 are proportionately reduced.

The condition of alarm latch 90 is sampled in synchronism with the application of power to sensing circuits 71 and 93, i.e. in synchronism with $V_{se}$. As previously noted, the Strobe signal 812E comprises 1.9 ms pulses (722, 734, 744) generated in sync with the sense enable pulses but occuring 5.9 ms after the onset of the sense enable pulses. Thus, latch 90 is strobed during periods while power is applied to the sensing systems, but only after the system components have had sufficient time to settle. The signal applied to the D input of latch 90 is reflected at the Q output thereof, AL, which is applied to control logic 70.

Control logic 70 generates the transducer control signal $T_r$ in accordance with the state of the AL signal from latch 90. More particularly, referring to FIG. 8, the alarm signal AL from latch 90 is applied through OR gate 822 to one input of AND gate 818. AND gate 818, which is selectively gated by the 39.1 ms pulses provided (at intervals of 97.7 ms) by the G output of counter/decoder logic 812, provides an output through OR gate 824 to AND gate 820. Accordingly, when the alarm signal AL is high, AND gate 820 generates respective groups of four 39.1 ms bursts of 2048 Hz repeated at 97.7 ms intervals. The output of AND gate 820 is applied to the gate of N channel FET 73 (FIG. 6) to selectively render FET 73 conductive and complete a current path for the coil 44C of transducer 44. Transducer 44, in cooperation with integral Helmholtz resonator 61, (FIG. 5), generates a singularly alerting sequence of sounds. The alarm sound includes a strong component of the basic frequency 2048 Hz generated by transducer 44, and in addition, a strong component of the second harmonic 4096 Hz amplified by Helmholtz resonator 61. As previously noted, this combination of frequencies includes at least one component which is discernable by people having various classes of hearing loss. The high second harmonic content of the produced sound is discordant, strident and piercing, thus enhacing the alerting nature of the sound.

In addition, the chopped nature of the alarm indicia (that is, the intermittent generation of groups of signal bursts) provides an additional alerting factor. It has been found that a continuous sound is not always sufficient to awaken a sleeper. However, an intermittent beep has been found, because of the change in audible conditions, to be considerably more alerting. An intermittent beep having a changing or interrupted beat (e.g. groups of four bursts repeated at 97.7 ms intervals, with the group repeated at 977 ms intervals) has been found to be more alerting still. In addition, the intermittent generation of signals provides substantial conservation of energy in respect of generating the alarm indicia. Thus, the useful life of battery 48 is increased.

The use of monitor 10 is briefly as follows. After fastening monitor 10 on his or her wrist, the wearer waits several minutes for the monitor to reach thermal stability. The wearer then momentarily presses control button 18. Depression of control button 18 initializes the circuitry and effects application of power to sensing systems 71 and 93. Monitor 10 then generates a single group of four short beeps, characteristic of completion of the Autoset function, signifying that a temperature reference has been established and stored and that no abnormal skin resistance exists. Periodically thereafter, monitor 10 updates the temperature reference and stores indicia of the updated reference to suppress effects of non-symptomatic slow temperature variations, while maintaining the required sensitivity to more rapid symptomatic temperature decreases. Once activated, monitor 10 will produce an alarm sound, a repeating series of groups of four signal bursts (beeps) upon detection of either decreased skin resistance or decreased skin temperature. The skin resistance and temperature conditions are reevaluated at intervals of approximately 5 seconds (4.9 seconds) for as long as the monitor is active. Monitor 10 can be deactivated only by intentional pressure on both control buttons 18 and 20 (located on opposite sides of case 12). Deactivating monitor 10 produces a single long beep sound (for the duration of the concurrent depression of the switches 18 and 20), signifying that the monitor has been deactivated.

More specifically, with reference to FIGS. 6, 7 and 8, the operation of monitor 10 in response to various conditions will be described. Table I below indicates responses to various typical temperature and skin resistance conditions.

TABLE 1

|  | Initial Power-Up | Normal Conditions | Temperature Alarm Condition | Abnormal Skin Resistance Condition | Silent Autoset |
|---|---|---|---|---|---|
| T | 33° C. | 33° C. | 31° C. | 33° C. | 35° C. |
| Rt | 34.3k | 34.3k | 37.7k | 34.3k | 31.2k |
| Rs | 215k | 215k | 215k | 165k | 215k |
| Sound | Auto-Set | None | Alarm | Alarm | None |

The signals associated with the operation of circuitry 40 under the conditions illustrated in Table I are illustrated in FIG. 7.

The various signals associated with initial power up and initialization of the system are shown in Division I of FIG. 7. As noted in Table I, a typical normal skin temperature is assumed in respect of Division I of FIG. 7. Accordingly, the resistance of thermistor 64 is assumed equal to 34.3kΩ. Skin resistance is assumed to be a normal value of 215kΩ.

Activation of monitor 10 is, as previously noted, initiated by momentary depression of switch 18. Timer control logic 70 responsively generates a low level signal $V_{de}$ to render FET 102 (FIG. 6) conductive and establish a high level signal $V_{dd}$ for application to the remainder of the circuitry. A Preset pulse 710 is then generated to establish a predetermined count, corresponding to minimum equivalent resistance $R_N$ (18.8kΩ). An Autoset pulse 714 then renders conductive FET 104 such that $V_{se}$ assumes the battery potential (2.8 volts) for the duration of the Autoset period (generally indicated as 716, FIG. 7). Comparator 76 then generates a high level signal 712 to enable AND gate 84 with respect to the clock signals from timer control logic 70 and counter 72 is enabled with respect to clock signals. The count is incremented from the preset value (e.g. binary equivalent of decimal 0) towards the maximum value (e.g., binary equivalent of 255). Counter 72 continues to increment until network 74 attains a resistance such that slightly less than $0.477V_{se}$ is dropped across thermistor 64. In this example, a typical count would be the binary equivalent of decimal 155. At that point, the output $A_t$ of comparator 76 goes low (falling edge 720), disabling AND gate 84. It is noted that the signal AA applied to the D input of alarm latch 90 is high during the period that the reference count is established in counter 72. However, as previously noted, alarm latch 90 is, in effect, inhibited by the Autoset pulse. Thus, the characteristic alarm indicia is not generated. However, counter/decoder 812 generates (at its B' output) a 391 ms pulse 721 to gate a series of four short signal bursts characteristic of the Autoset, as previously explained.

After the termination of the Autoset period, monitor 10 enters what may be termed a sampling (sensing) mode of operation. The signals associated with the sampling mode operation under normal conditions, decreased temperature conditions, and decreased skin resistance conditions, are illustrated in Divisions II, III and IV of FIG. 7, respectively. As previously mentioned, the Sense Enable signal comprises a 7.8 ms pulse generated at 4.9 second intervals. Accordingly, the $V_{se}$ power signal applied to sensing systems 71 and 93 track the Sense Enable signal, that is, the power signal comprises 2.8 volt pulses of 7.8 ms duration occurring at intervals of 4.9 seconds. Upon the termination of the Autoset signal, the reference voltage $V_{To}$ applied to comparator 76 assumes a value of $0.500V_{se}$, corresponding to a temperature 2° C. lower than the temperature reflected by the count in counter 72.

Under normal conditions, as reflected in Division II, skin temperature is, for example, 33° C. and skin resistance is over 200kΩ, e.g. 215kΩ. The voltage drop across thermistor 64 is less than $0.500V_{se}$, and the output $A_t$ of comparator 76 is low. Similarly, the voltage drop across the skin resistance is greater than $0.500V_{se}$ and the output $A_r$ of comparator 96 is also low. The signal AA applied to the data input of alarm latch 90 is therefor also low.

Latch 90 is clocked in synchronism with the Sense Enable signal by the strobe signal. As previously noted, the strobe signal comprises a 1.9 ms pulse 722 occurring synchronously with the Sense Enable but delayed 5.9 ms with respect to the onset of Sense Enable pulse. More particularly, the strobe occurs during the Sense Enable pulse but after a sufficient period to ensure that sensor systems 71 and 93 have settled after application of the $V_{se}$ pulse. Under normal conditions, the alarm signal AL applied to control logic 70 is low level and no alarm indicia is at a generated.

However if an abnormal temperature drop occurs, i.e. the temperature drops to 31° C. as reflected in Division III of FIG. 7, the resistance of thermistor 64 increases by approximately 9.4% (4.7% per °C.). The voltage drop across thermistor 64 exceeds $0.500 V_{se}$, causing the output $A_t$ of comparator 76 to develop a positive pulse 730. Accordingly, the signal AA applied to alarm latch 90 exhibits a concomitant pulse 732. When a strobe signal pulse 734 subsequently occurs, the outut AL of alarm latch 90 will assume a positive value as indicated at 736.

Accordingly, timer control logic 70 generates signal $T_r$ to FET 73 to effect operation of transducer 44 to generate the chopped bursts of signal characteristic of the alarm indicia, generally indicated at 738. The high value of the AL signal, and thus the alarm indicia, is maintained until the next successive strobe signal (or longer if the condition is not remedied).

Similarly, where a decreased skin resistance condition occurs, as reflected in Division IV of FIG. 7, that is, perspiration occurs on the skin causing the skin resistance $R_s$ to decrease to a value below 200kΩ, e.g. 165kΩ, the voltage drop across the skin resistance $R_s$ decreases to below $0.500V_{se}$. Accordingly, the output $A_r$ of comparator 96 exhibits a positive pulse 740. Accordingly, a positive pulse 742 is provided at the D input of latch 90. When the next strobe signal 744 occurs, the output AL of alarm latch 90 assumes a high level value, indicated at 746, causing generation of the characteristic alarm indicia as indicated at 748.

As previously noted, relatively slow nonsymptomatic variations in temperature are compensated for by periodically adjusting the temperature reference. Accordingly, as illustrated in Division V of FIG. 7, the Preset and Autoset pulses are repeated at predetermined intervals, e.g. every 20.8 minutes (indicated at 750 and 752 respectively). For the purposes of illustration, it is assumed that over the course of the 20.8 minute period, the skin temperature increased by two degrees to 35° C. The Sense Enable signal causes a 2.6 volt pulse 754 of 391 ms duration to occur in $V_{se}$. The temperature reference $V_{To}$ assumes, for the duration of the Autoset pulse, a value of $0.477V_{se}$, and counter 72 is preset enabled with respect to the clock pulses from control logic 70. Accordingly, counter 72 accumulates a count until the voltage across thermistor 64 attains a $0.477V_{se}$ value, whereupon counter 72 is disabled (at a count equivalent to approximately decimal 137). Again, it is noted that the output of comparator 76 is high during the accumulation of the reference temperature count in counter 72, and thus, a high level signal is applied to the D input of latch 90. However, during the Autoset period latch 90 is held in a reset condition and no alarm signal is generated. The periodic Autoset differs from the initial power up Autoset in that no audible indication is generated. Counter/decoder logic 812 output B' produces no pulse to provide for gating of signals to FET 73 to actuate transducer 44.

Deactivation of monitor 10 is illustrated in Division VI of FIG. 7. As previously noted, deactivation is effected by concurrently depressing switches 18 and 20. Concurrent depression of switches 18 and 20 causes NAND gate 814 to generate a positive going signal to reset flip flop 810 and thus cause $V_{de}$ to go high (shown at 772). Accordingly, FET 102 is rendered nonconductive and signal $V_{dd}$ assumes a low value (shown at 774). In addition, AND gate 820 is enabled with respect to the 391 ms bursts of 2048 Hz signal generated at output F of counter/decoder logic 812. Accordingly, FET 91 is selectively rendered conductive to cause transducer 44 to generate concomitant signal bursts as indicated schematically at 776, to signify to the wearer that monitor 10 has been deactivated.

It will be understood that while various of the conductors and connections are shown in the drawing as single lines they are not so shown in a limiting sense, and may comprise plural connections as is understood in the art. Further, the above description is of a preferred exemplary embodiment of the present invention and is not limited to the specific forms shown.

For example, the function of timer control logic 70, the respective gates 84, 86, 88, 100 and 106, and latch 90 could be performed by a suitable microprocessor. Also, while the preferred exemplary embodiment detects decreases in temperature and resistances, the monitor can readily be adapted, if desired, to detect increases in temperature or resistance. These and other modifications can be made in the design and arrangement of the elements without departing from the spirit of the invention as expressed in the appended claims.

What is claimed is:

1. Apparatus for physiological monitoring of a subject comprising:

temperature sensing means for generating a temperature signal indicative of the temperature therof, said temperature sensing means including a thermistor having a predetermined temperature coefficient;

means for disposing said temperature sensitive means in thermal contact with said subject;

reference means, responsive to control signals applied thereto, for selectively generating a temperature reference signal indicative of a threshold temperature, said reference means including:

storage means for controllably storing indicia of the instantaneous temperature, as a stored reference temperature, said threshold temperature being in predetermined relation with said stored reference temperature, and accumulator means, responsive to enable control signals and clock signals applied thereto, for selectively accumulating a count when enabled and controllably storing said count;

digital to analog converter means, responsive to said count, for providing a current to said thermistor to develop a temperature voltage across said thermistor indicative of the instantaneous temperature, the magnitude of said current varying in accordance with said count;

temperature comparison means, responsive to said temperature signal and said temperature reference signal, for generating a temperature comparison signal indicative of a comparison between said temperature and reference signals;

means, responsive to control signals applied thereto, for alternatively generating at least an accumulation reference voltage and a threshold reference voltage to said comparison means, said threshold reference voltage differing from said accumulation reference voltage in accordance with said predetermined relation between said threshold temperature and said stored reference temperature;

gating means, responsive to said comparison signal, for selectively applying said clock signals to said accumulator means;

alarm means, responsive to said temperature comparison signal, for selectively generating alarm indicia; and control means for generating said control signals to said reference means to effect storage of said temperature indicia;

wherein said control means generates control signals to effect generation of said accumulation reference voltage during periods when said accumulator means is enabled such that said count is accumulated until the instantaneous temperature voltage is approximately equal to said accumulation reference voltage, said accumulation voltage thereby being equated to said stored reference temperature and said threshold reference voltage being equated to said threshold temperature, said control means also generating control signals to effect generation of said threshold reference voltage during periods when said count is stored.

2. The apparatus of claim 1 further comprising:

resistance sensing means for generating a resistance signal indicative of the galvanic skin resistance of said subject, and resistance comparison means for generating a resistance comparison signal indicative of a comparison between said resistance signal and a predetermined resistance reference signal;

said resistance comparison signal being applied to said alarm means to selectively effect generation of alarm indicia.

3. The apparatus of claim 1 further including means for intermittently applying power to said digital to analog converter means, and said means for generating said reference voltages; and wherein said alarm means includes means for sampling said comparison signal in synchronism with said intermittent application of power.

4. The apparatus of claim 1 wherein said means for disposing said temperature sensing means in thermal contact with said subject comprises:

a case, including a thermally conductive portion and means for thermally insulating said thermally conductive portion from adjacent portions of said case, said thermistor being disposed in thermal contact with said thermally conductive portion;

means for disposing said thermally conductive portion in thermal contact with said subject; and a resilient thermally insulative element, comprising first and second electrically conductive protions and an electrically nonconducting portion interposed therebetween for maintaining said thermistor in contact with said thermally conductive case portion and effecting electrical connections between said thermistor and said digital to analog converter means.

5. Apparatus for physiological monitoring of a subject comprising:

temperature sensing means for generating a temperature signal indicative of the temperature thereof, said temperature sensing means comprising a thermistor;

means for disposing said temperature sensitive means in thermal contact with said subject;

reference means, responsive to control signals applied thereto, for selectively generating a temperature reference signal indicative of a threshold temperature, said reference means including storage means for controllably storing indicia of the instantaneous temperature, as a stored reference temperature, said threshold temperature being in predetermined relation with said stored reference temperature;

temperature comparison means, responsive to said temperature signal and said temperature reference signal, for generating a temperature comparison signal indicative of a comparison between said temperature and reference signals;

alarm means, response to said temperature comparison signal, for selectively generating alarm indicia; and control means for generating said control signals to said reference means to effect storage of said temperature indicia, wherein said reference means comprises:

a counter, responsive to enable control signals of predetermined duration and clock signals applied thereto, for controllably accumulating a count when enabled and controllably maintaining said count;

variable resistance means, serially connected with said thermistor, for presenting a resistance corresponding to said count;

variable voltage divider means, responsive to said enable signal, for providing said temperature reference voltage in accordance with a first ratio of resistances in response to said enable signal, and in accordance with a second ratio of resistances in the absence of said enable signal; and gating means, responsive to said comparison signal, for controllably applying clock signals to said counter in accordance with said comparison such that a count corresponding to said first ratio of resistances to the instantaneous temperature of said thermistor is accumulated and controllably maintained.

6. The apparatus of claim 5 wherein said reference means comprises:

means for accumualting a count during at least one accumulation period and controllably maintaining said count;

means, responsive to said count, for varying the correspondence of said temperature signal to temperature level in accordance with said count;

means for periodically incrementing said count during said accumulation period until correspondence between said temperature signal and a first reference signal is attained; and means for generating a second reference signal having a predetermined relationship with said first reference signal in accordance with said predetermined relation between said threshold and stored reference temperatures, for application to said comparison means as said temperature reference signal.

7. The apparatus of claim 5 further comprising a resilient thermally insulative element including first and second electrically conductive portions and an electrically non-conductive portion separating said conductive portions, for effecting electrical connections between said thermistor and said variable resistance means.

8. Apparatus for physiological monitoring of a subject comprising:

temperature sensing means for generating a temperature signal indicative of the temperature thereof;

means for disposing said temperature sensitive means in thermal contact with said subject;

reference means, responsive to control signals applied thereto, for selectively generating a temperature reference signal indicative of a threshold temperature, said reference means including storage means for controllably storing indicia of the instantaneous temperature, as a stored reference temperature, said threshold temperature being in predetermined relation with said stored reference temperature;

temperature comparison means, responsive to said temperature signal and said temperature reference signal, for generating a temperature comparison signal indicative of a comparison between said temperature and reference signals;

alarm means, responsive to said temperature comparison signal, for selectively generating alarm indicia;

control means for generating said control signals to said reference means to effect storage of said temperature indicia; and a resilient thermally insulative element including at least one electrically conductive portion for effecting electrical connections between said temperature sensing means and at least one of said reference means and said temperature comparison means.

9. The apparatus of claim 8 wherein said resilient element includes first and second electrically conductive portions and an electrically non-conductive portion separating said conductive portions.

10. The apparatus of claim 4, 7, or 9 wherein said resilient thermally insulative first and second electrically conductive portions and said electrically non-conductive portion are coaxial.

11. Apparatus for physiological monitoring of a subject comprising:

a thermistor having a predetermined temperature characteristic;

means for disposing said thermistor in thermal contact with said subject;

a counter, responsive to enable control signals of predetermined duration and clock signals applied thereto, for controllably accumulating a count when enabled and controllably maintaining said count;

variable current generator means, serially connected with said thermistor, for presenting a current to said thermistor having a magnitude corresponding to said count;

variable voltage divider means, responsive to said enable signal, for providing a reference voltage in accordance with a first ratio of resistances in response to said enable signal, and in accordance with a second ratio of resistances in the absence of said enable signal;

comparison signal in accordance with a comparison between said thermistor voltage drop and said reference voltage;

gating means, responsive to said comparison signal, for controllably applying clock signal to said counter in accordance with said comparison such that a count corresponding said first ratio of resistances to the instantaneous temperature of said thermistor is accumulated and controllably maintained;

alarm means, responsive to said comparison signal, for selectively generating alarm indicia; and control means for selectively generating said enable signals.

12. The apparatus of claim 11 wherein said control means comprises means for generating said enable signals on a periodic basis to periodically update said count.

13. The apparatus of claim 11 where said control means comprises means for generating said enable signals at predetermined intervals.

14. The apparatus of claim 11 further comprising;

resistance sensing means of generating a resistance signal indicative of the galvanic skin resistance of said subject; and resistance comparison means for generating a resistance comparison signal indicative of a comparison between said resistance signal and a predetermined resistance reference signal;

said resistance comparison signal being applied to said alarm means to selectively effect generation of alarm indicia.

15. The apparatus of claim 11 further including means for intermittently applying power to said thermistor, variable resistance means and variable voltage divider means; and wherein said alarm means includes means for sampling said comparison signal in synchronism with said intermittent application of power.

16. Apparatus for physiological monitoring of a subject comprising:

a case, including an electrically conductive underside adapted for electrical contact with said subject; said underside including an aperture therein;

temperature sensing means, including a temperature sensitive element and disposed within said case, for generating a temperature signal indicative of temperature;

an electrically and thermally conductive cap; adapted to receive said temperature sensitive element in electrical and thermal contact with the interior thereof;

retainer means for securing said cap in said underside aperture, to dispose said cap for electrical and thermal contact with said subject, electrically and thermally isolated from said underside;

means for providing electrical connections to said temperature sensitive element and said cap;

resistance sensing means, electrically connected to said underside and said cap, for generating a resistance signal indicative of the galvanic skin resistance of said subject; and alarm means, responsive to said temperature signal and said resistance signal for generating alarm indicia in response to predetermined physiological conditions of said subject.

17. The apparatus of claim 16 wherein said means for providing electrial connections comprises a resilient element formed of thermally insulated material and including at least one electrically conductive portion.

18. The apparatus of claim 17 wherein said resilient element includes first and second electrically conductive portions, and an electrically non-conductive portion separating said electrically conductive portions.

19. The apparatus of claim 18 wherein said first and second electrically conductive portions and said electrically non-conductive portions are coaxially disposed.

20. The apparatus of claim 19 wherein said temperature sensitive element includes first and second terminals said first terminal being adapted for electrical contact with said cap and said second terminal being disposed removed from said cap, wherein said resilient element first electrically conductive portions is adapted for electrical contact with said cap and said resilient element second electrically conductive portion is adapted for contact with said second terminal, said resilient element electrically non-conductive portions electrically isolating said first and second terminals.

21. The apparatus of claim 16 wherein said alarm means includes:

transducer means for controllably generating audio tones;

an enclosure, disposed to receive said tones and present a predetermined volume of air to said transducer;

at least one aperture, communicating between said enclosure and the exterior of said case, said aperture having a volume in predetermined relationship to said enclosure volume.

22. The appartus of claim 16 wherein said resistance sensing means includes means for intermittently generating a current for passage between said cap and said underside.

23. The apparatus of claim 22 wherein said alarm means includes means for responding to said resistance sensing means in synchronism with said intermittent current.

24. The apparatus of claim 16 wherein: said temperature sensing means includes:

means, responsive to control signals applied thereto, for storing indicia of a reference temperature; and means for generating said control signals to said means for storing at predetermined intervals to effect storing of an updated reference temperature; and said alarm means includes means for comparing sensed temperature to a threshold temperature having a predetermined relationship to said reference temperature and generation said alarm indicia in accordance with said comparison.

25. The apparatus of claim 16 further including a static charge protection capacitor electrically connected to one of said cap and underside.

26. Apparatus for physiological monitoring of a subject comprising:

temperature sensing means for generating a temperature signal indicative of the temperature thereof, said temperature sensitive means comprising a thermistor;

means for disposing said temperature sensitive means in thermal contact with said subject;

reference means, responsive to control signals applied thereto, for selectively generating a temperature reference signal indicative of a thresold temperature, said reference means including storage means for controllably storing indicia of the instantaneous temperature, as a stored reference temperature, said threshold temperature being in predetermined relation with said stored reference temperature;

temperature comparison means, responsive to said temperature signal and said temperature reference signal, for generating a temperature comparison signal indicative of a comparison between said temperature and reference signals;

alarm means, responsive to said temperature comparison signal, for selectively generating alarm indicia; and control means for generating said control signals to said reference means to effect storage of said temperature indicia, wherein said reference means comprises:

a counter, responsive to enable control signals of predetermined duration and clock signals applied thereto, for controllably accumulating a count when enabled and controllably maintaining said count;

variable current generator means for applying a current to said thermistor having a magnitude in accordance with said count;

variable voltage divider means, responsive to said enable signal, for providing said temperature reference voltage in accordance with a first ratio of resistances in response to said enable signal, and in accordance with a second ratio of resistances in the absence of said enable signal; and gating means, responsive to said comparison signal, for controllably applying clock signal to said counter in accordance with said comparison such that a count corresponding to said first ratio of resistances to the instantaneous temperature of said thermistor is accumulated and controllably maintained.

* * * * *